(12) United States Patent
Mehrer

(10) Patent No.: US 7,632,949 B2
(45) Date of Patent: Dec. 15, 2009

(54) PROCESS FOR THE PREPARATION OF STABILIZERS FOR POLYMERS

(75) Inventor: Mathias Mehrer, Gablingen (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 662 days.

(21) Appl. No.: 10/525,149

(22) PCT Filed: Aug. 15, 2003

(86) PCT No.: PCT/IB03/03718

§ 371 (c)(1),
(2), (4) Date: Feb. 16, 2006

(87) PCT Pub. No.: WO2004/016591

PCT Pub. Date: Feb. 26, 2004

(65) Prior Publication Data

US 2006/0199963 A1    Sep. 7, 2006

(30) Foreign Application Priority Data

Aug. 19, 2002 (GB) .................................. 0219260.7

(51) Int. Cl.
*C07D 401/10* (2006.01)
(52) U.S. Cl. .................................................. 546/187
(58) Field of Classification Search .................. 546/187
See application file for complete search history.

(56) References Cited

U.S. PATENT DOCUMENTS

| | | | |
|---|---|---|---|
| 4,003,875 A | 1/1977 | Luthi et al. | 252/589 |
| 4,544,691 A | 10/1985 | Dexter et al. | 524/99 |
| 5,045,083 A | 9/1991 | Bennett | 8/442 |
| 5,338,319 A | 8/1994 | Kaschig et al. | 8/586 |
| 5,380,774 A | 1/1995 | Mulholland | 524/182 |
| 6,063,843 A | 5/2000 | Sidqi et al. | 524/100 |

FOREIGN PATENT DOCUMENTS

| | | |
|---|---|---|
| EP | 0903372 | 3/1999 |
| EP | 1000967 | 5/2000 |
| GB | 2311292 | 9/1997 |
| WO | WO 97/43335 | 11/1977 |

OTHER PUBLICATIONS

Lee et al. "Syntheses of some new . . . " CA 79:105051 (1973).*
PCT ISR for PCT/IB03/03718, mailed Nov. 24, 2003.
English Abstract for JP 07033738, Feb. 3, 1995.
KW Lee et al.; "Synthesis of Some New Compounds Containing Stable Free Radicals," Hwahak Konghak, vol. 11, No. 1, pp. 15-22, XP009019713 (1973).
Ferruti et al.; "Synthesis of Nono-, di-, and Polynitroxides," Journal of the American Chemical Society, vol. 92, No. 12, pp. 3704-3713; XP002260936 (1970).
PCT IPER for PCT/IB03/03718, Jun. 11, 2004.

* cited by examiner

*Primary Examiner*—Celia Chang
(74) *Attorney, Agent, or Firm*—Anthony A. Bisulca

(57) ABSTRACT

The instant invention relates to a process for the preparation of stabilizers for polymers, especially for polyamides, by condensation of isophthalic acic dichloride (IPC) with sterically hindered amines of the type tetraalkylpiperidine. By using organic solvents or mixtures of organic solvents with water and by an optimized combination of temperature and pressure the yield is much higher than by using water alone. The organic load of the waste water could be significantly reduced.

8 Claims, No Drawings

PROCESS FOR THE PREPARATION OF STABILIZERS FOR POLYMERS

The instant invention relates to a process for the preparation of stabilizers for polymers, especially for polyamides.

The service life of polyamides is dependent on the raw materials used within the manufacturing process, the additives used in stabilizing the polymer against damage brought about by melt-processing and environmental weathering factors. A serious drawback to providing stabilization systems for polyamides lies in the fact that maximum concentration of many additives is limited. Polyamides are regarded as poor in solvating additives, especially non-polar additives having relatively low molecular weight in relation to the polyamide polymer. On the other hand, manufacturers of polyamide-based molded and extruded goods strive to include low concentrations of additives for economic reasons.

Some of the stabilizers or stabilizer systems which are used for stabilization of polyamide are mentioned for example in U.S. Pat. No. 4,003,875 (unsymmetrical oxalic acid dianilides), U.S. Pat. No. 5,045,083 (copper complexes and oxanilide UV absorbers), U.S. Pat. No. 4,544,691 (oxalanilides, benzalmalonates, α-cyanocinnamates and o-hydroxyphenylbenzotriazoles), U.S. Pat. No. 5,338,319 (copper complex and oxalic acid diaryl amide) or U.S. Pat. No. 5,380,774 (hindered phenolic antioxidant, phosphite, hindered amine stabilizer and optionally a benzotriazole).

Polyamide polymers are characterized by high tensile strength, abrasion resistance, however polyamides require also stabilization against thermo-oxidative and photodegradation to sustain these properties in their long-term applications.

Polyamides must accept lightfast dying systems in addition. Discoloration of the matrix is regarded to be highly critical and may cause shade changes in colored articles, e.g. fibres and moldings of polyamide polymers.

Therefore further improvement in the stabilization systems of polyamide polymers is always needed.

The most powerful stabilizer generally used for the stabilization of polyamides first mentioned in WO 97/43335 can be seen in general formula (I) (definition of radicals see below)

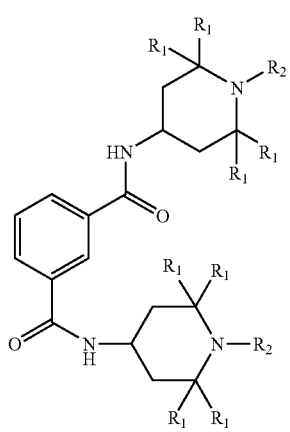

(I)

This powerful stabilizer can be added in the melt of polyamides and improves heat stability, light stability, chemical stability and dye affinity of the polyamide polymer.

In the meantime new stabilizer systems were found which combine the unique properties of (I) in synergistic combinations together with other additives. Examples therefore can be found in EP 0903372 A1 or U.S. Pat. No. 6,063,843. Compound (I) or derivatives thereof can also successfully be used for the stabilization of polyester resins as can be seen in EP 1000967 A1.

Originally, stabilizers of general formula (I) were synthesized by condensation of isophthalic acic dichloride (IPC) with sterically hindered amines of general formula (II), where radicals $R_1$ and $R_2$ are defined below. Water was used as a solvent for this reaction.

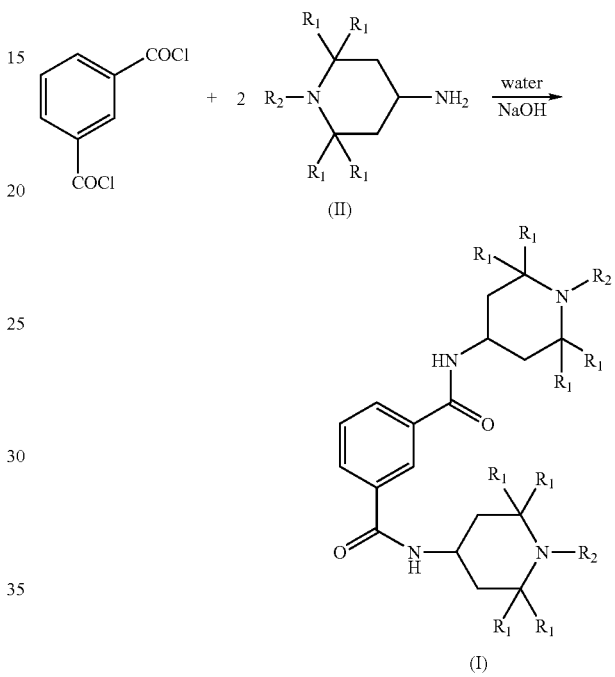

For achieving acceptable yields, excess of the amine component (II) had to be used.

Amine components of general formula (II) are generally known to be poorly biodegradable.

As the excess of the amine component had to be washed out after reaction with water, waste water was produced which cannot be treated effectively in conventional sewage plants.

The yields which could be achieved by the above mentioned process were limited, due to hydrolysis with water which occurred during reaction phase.

Thus this process known from the prior art could not be transferred to a regular production plant, due to the mentioned disadvantages.

GENERAL DESCRIPTION OF THE INVENTION

It has now been found that the use of certain organic solvents together with an optimized combination of pressure and temperature leads to a surprising increase of the overall yield of more than 10% and to less environmental problems by a reduced organic load of the waste water.

Therefore object of the instant invention is a process for the preparation of stabilizers of general formula (I) by condensation of isophthalic acic dichloride (IPC) with sterically hindered amines of general formula (II),

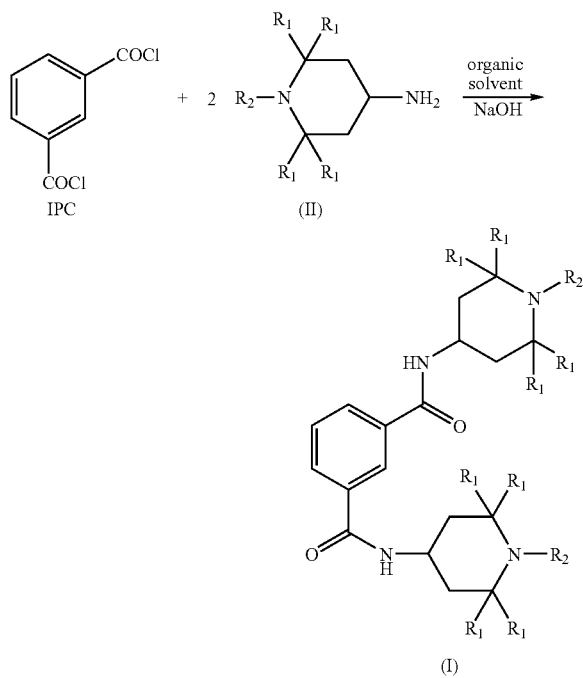

wherein $R_1$ is H, $C_6$-cycloalkyl or $C_1$-$C_4$-alkyl, and $R_2$ is H, $C_1$-$C_5$-alkyl, or a $C_1$-$C_{10}$-alkyloxy-group, characterized in that organic solvents or mixtures thereof with water and an optimized combination of pressure and temperature are used during the whole process.

Preferably $R_1$ is H or $C_1$-$C_2$-alkyl and $R_2$ is H or $C_1$-$C_2$-alkyl, most preferably $R_1$ is methyl and $R_2$ is H.

The reaction between IPC and component (II) is carried out by stirring IPC into a solution containing compound (II), 30-70%, preferably 40-60%, most preferably 50% by weight of aqueous caustic soda, organic solvent and water.

One key step of the invention is the use of organic solvents or mixtures of organic solvents with water instead of water alone as in the prior art. The solvents used are organic aromatic hydrocarbons, preferably xylene, or aliphatic alcohols, preferably ethanole or isopropanole. Most preferably isopropanole or mixtures of isopropanole with water are used.

The preferred ratio of isopropanole to water is from 60-80% isopropanole to 20-40% water, most preferably the ratio is 70% isopropanole and 30% water by volume.

By using mentioned solvents or mixtures of these solvents with water, the yield could be improved from 85% to 96% of theory; that means that hydrolysis-reaction could be minimized.

Also the excess of the bio-toxical amine component (II) could be avoided without reducing yield. The instant process uses a molar ratio of IPC and the amine component (II) of 1 mole IPC to 1.80-2.00 mole of (II), preferably 1.80-1.90 mole of (II), most preferably a molar ratio of 1 mole IPC to 1.85 mole of (II) is applied. This leads to a minimum organic load of waste water, which has significant advantages in respect to the mentioned biotoxical properties of component (II).

However the instant solvent system alone cannot eliminate completely the problems of the process of the prior art. Even by using mixtures of water and an organic solvent at ambient pressure, (I) is isolated as small, sticky, cake-like particles, which cannot be isolated easily on conventional filtration aggregates like centrifuges or suction filters. As consequence big amounts of water had to be applied in order to wash effectively and to reach acceptable product quality.

Therefore a further key of this invention is the instant combination of reaction conditions like temperature and pressure. Thereby as a further advantage filtration properties of the crystals of the compound of general formula (I) could be improved significantly.

Addition of IPC to the amine (II) in the solvent/water/NaOH solution is performed at temperatures from 2040° C., preferably 25-35° C., most preferably at 30° C.

After addition of IPC has completed, the reaction mixture is stirred for 50 to 70 minutes, preferably for one hour at the same temperature. The reaction mixture is then heated in an autoclave to 90-110 ° C., preferably to 100° C. and to a system pressure of 1.3 to 1.7 bars, preferably of 1.5 bars. Under these conditions the reaction product is completely dissolved in the solvent and 2 phases can easily be separated.

The aqueous layer which contains most of the salts, excess of caustic and some residues of isopropanole, can be easily separated and—after redistillation of the residual solvent—be further treated in a conventional sewage plant.

After addition of water, the organic layer is heated to a temperature of 130-140° C. and a system pressure of 3.0-4.0 bars until all of the solid has dissolved. The reaction mixture now is cooled to ambient temperature and large crystals of products of general formula (I) are formed, which can be isolated by using conventional filter aggregates.

By using the instant process, the yield of the reaction could be raised to 96%, waste water consumption and load could be reduced significantly and the filtration properties of the reaction product formed could be optimized, which leads to maximum output of products of formula (I) in a regular production plant. The instant process therefore is ecologically advantageous.

The instant process leads to stabilizers of general formula (I), which can also be used in stabilizer systems as indicated in U.S. Pat. No. 6,063,843. Also further additives can be added according to different applications. These further additives are also described in U.S. Pat. No. 6,063,843.

EXAMPLES

The given examples shall illustrate the advantage of the novel process for preparation of stabilizers of general formula (I). Examples are used, where radicals $R_1$=methyl, and $R_2$=H. The stabilizer of formula (I) with $R_1$=methyl, and $R_2$=H is generally well-known as a powerful stabilizer for polyamide polymers and commercialized by Clariant under the brand name Nylostab® S-EED®.

Example 1

In a 4-necked 2 l flask with stirrer, dropping funnel, thermometer and pH electrode 150.5 g of 2,2,2,6-Tetramethylpiperdin-4-amine (98.7%; 0.95 mole) and 85.2 g of 50% NaOH solution (1.07 mole) are added to a mixture of 470.0 g of isopropanol and 260.0 g of demin. water.

Until Stirring 102.1 g of molten isopthalic acid chloride (99.4%; 0.50 mole) are added The temperature of the reaction mixture is held at 30° C. during dosage of IPC by cooling with an ice bath. The reaction mixture is stirred for another 1 hour under the same conditions (temperature/pH-control). A-white suspension is being formed during this reaction phase. The reaction mixture is transferred to a 3 l laboratory autoclave with stirrer and internal thermometer and the mixture is heated to a temperature of TI=100° C. The resulting pressure of the system is about 1.5 bar and the solid is being dissolved completely.

Two liquid phases are being formed:
Lower aqueous phase containing salts and aqueous NaOH and some isopropanole
Upper organic phase containing desired product solved in isopropanole;
The lower phase is removed under pressure and
950.0 g of demin. water is added to the reaction mixture.

The mixture is further heated up to TI=130° C. and a corresponding system pressure of about PI=3.3 bar until all of the solid has completely dissolved. The suspension is allowed to cool down to ambient temperature TI≈30° C. The resulting white suspension is passed through a filter aggregate with metal screen and the reaction product is washed with 715.0 g of demin. water to remove chloride and other impurities. The reaction product is heated in a vacuum drying oven until constancy of weight. The yield of reaction product of general formula (I) with $R_1$=methyl, and $R_2$=H is 200.0 g or 95.3% of theoretical value (yield based on minor component TAD).

Example 2 (Comparison Example)

In a 4-necked 2 l flask with stirrer, dropping funnel, thermometer and pH electrode
161.2 g of 2,2,6,6-Tetramethylpiperdine-4-yl-amine (98.7%; 1.02 mole) and
93.2 g crushed ice
are cooled to a temperature of 7° C.
Under stirring
102.1 g of molten isophthalic acid chloride (99.4%; 0.50 mole) are added.

The temperature of the reaction mixture is held below 10° C. during dosage of IPC. After addition of IPC the sticky mass is diluted with
450.0 g of demin. water and
133.3 g of 30% NaOH (1.00 mole) is added.
During addition of NaOH
300.0 g of demin. water is added to dilute the reaction mass.

After 3 h of stirring at 25° C. the sticky suspension is filtered on a laboratory suction filter and washed until the pH reaches a value of 10 (in total 2400 g of demin. water are needed).

The filter cake again is suspended in
600.0 g of demin. water, stirred for 30 min and again is isolated on a laboratory suction filter and washed with 700.0 g of demin. water.

The reaction product is heated in a vacuum drying oven until constancy of weight. The yield of reaction product of general formula (I) with $R_1$=methyl, and $R_2$=H is 184.8 g or 83.6% based on IPC.

TABLE 1

Main Results of Examples 1 (Novel Process) and Comparison Example 2 (Old Process):

|  | Example 1 | Example 2 |
|---|---|---|
| Amount (TAD*) g/batch | 150.5 | 161.2 |
| Yield of (I) g; % | 200.0; 95.3 | 184.8; 83.6 |

TABLE 1-continued

Main Results of Examples 1 (Novel Process) and Comparison Example 2 (Old Process):

|  | Example 1 | Example 2 |
|---|---|---|
| Filtrate 1 amount (g) | 524.0 | 438.6 |
| COD** mg/l | 12000 | 45000 |
| TAD filtrate 1 (g) | none | 0.5 |
| Waste Water 1 amount (g) | 328.5 | 2363 |
| COD** mg/l | 5200 | 5000 |
| TAD in waste water 1 (g) | none | 0.03 |
| Filtrate 2 amount (g) | none | 690 |
| COD** mg/l | none | 1900 |
| TAD filtrate 2 (g) | none | 0.002 |
| Waste Water 2 amount (g) | none | 2800 |
| COD** mg/l | none | 1300 |
| TAD in waste water 2 (g) | none | none |

*TAD: 2,2,6,6-Tetramethylpiperidin-4-yl-amine
**COD: Chemical oxygen demand: oxygen equ. needed for oxidation of organic load in waste water As can be seen in table 1, the amount of TAD/batch needed for reaction in example 1 is significantly lower than in example 2. Nevertheless, the isolated yield of reaction product of formula (I) is about 12% higher than in example 2.

The amount of waste water needed as well as the amount of residual TAD in waste water is much lower in comparison to example 2 as can be seen in table 1. Therefore the novel inventive process not only means a progress in respect to the advantageous reaction conditions in example 1, but also in respect to the waste water consumption and load being produced.

Example 3

The filtration properties of crystals of the reaction product (I) with radicals $R_1$=methyl, and $R_2$=H of examples 1 and 2 were tested on a standard filtration unit. This unit consists of a steel pressure filter (I=0.5 m; d=0.05 m; Co. BHS; metal screen porosity 60 μm). The filter unit is filled with a standard volume (800 ml) of the product suspension of (I). The filter unit is closed and a pressure of 1 bar $N_2$ is applied. The filtration time is measured as a function of the volumes of filtrate being produced during filtration. A good filtration time correlates with good filtration properties of the suspension:

TABLE 2

Filtration properties of the product suspension of (I) on a standard BHS filter-unit

| | time (s) Filtrate | | | |
|---|---|---|---|---|
| | 100 ml | 200 ml | 300 ml | 400 ml |
| example 1 | 3 | 11 | 22 | 35 |
| example 2 | 40 | 175 | 370 | 470 |

As can be seen in table 2, the filtration properties of the suspension of example 1 are much better compared to the filtration properties of suspension in example 2. As this results correlate with the filtration properties on a regular production filter aggregate, a much higher capacity can be achieved by using the new production process.

The invention claimed is:
1. A process for the preparation of a stabilizer of formula (I) comprising the step of reacting, by condensation, isophthalic acic dichloride with a sterically hindered amine of formula (II),

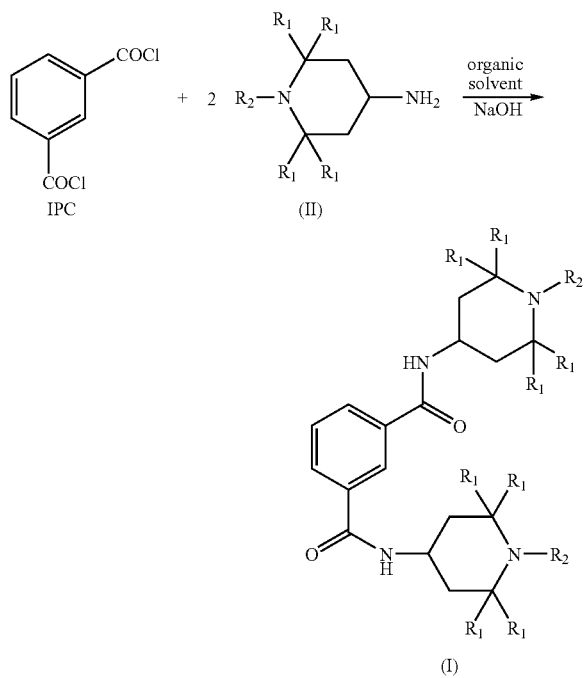

wherein $R_1$ is H, $C_6$-cycloalkyl or $C_1$-$C_4$-alkyl, and $R_2$ is H, $C_1$-$C_5$-alkyl, or a $C_1$-$C_{10}$-alkyloxy-group, wherein the reacting step includes adding the isophthalic acic dichloride to the amine in a solution of at least one organic solvent, water and NaOH at a temperature of 25 to 35° C. to form a reaction mixture, and heating the reaction mixture in an autoclave to a temperature of 90-110° C. at a system pressure of 1.3-1.7 bars, wherein the organic solvent is selected from an aromatic hydrocarbon and an aliphatic alcohol.

2. The process according to claim 1 wherein $R_1$ is H or $C_1$-$C_2$-alkyl and $R_2$ is H or $C_1$-$C_2$-alkyl.

3. The process according to claim 1 wherein $R_1$ is methyl and $R_2$ is H.

4. The process according to claim 1, wherein the molar ratio of the isophthalic acic dichloride to the amine from 1 to 1.8-2.0.

5. The process according to claim 1, wherein the at least one solvent is xylene, ethanole isopropanole or a mixture of 60-80% isopropanole and 20-40% water by volume.

6. The process according to claim 1, wherein the adding step further comprises stirring the mixture for 50 to 70 minutes while maintaining the same temperature.

7. The process according to claim 1, wherein a phase separation occurs after the heating step to form an organic phase and wherein the process further comprises adding water to the organic phase and heating the water and organic phase to a temperature of 130-140° C. at a pressure of 3.0-4.0 bars.

8. The process according to claim 1, comprising the step of cooling the reaction mixture to ambient temperature and isolating the compound of formula (I).

* * * * *